United States Patent [19]

Skrzec

[11] 4,436,673
[45] Mar. 13, 1984

[54] FLUID BED PROCESS FOR PREPARING PHENYLPHOSPHONOUS DICHLORIDE

[75] Inventor: Adam E. Skrzec, West Nyack, N.Y.

[73] Assignee: Stauffer Chemical Company, Westport, Conn.

[21] Appl. No.: 199,793

[22] Filed: Oct. 23, 1980

[51] Int. Cl.³ .............................................. C07F 9/42
[52] U.S. Cl. .............................................. 260/543 P
[58] Field of Search ..................................... 260/543 P

[56] References Cited

U.S. PATENT DOCUMENTS

| | | | |
|---|---|---|---|
| 3,029,282 | 4/1962 | Toy et al. | 260/543 |
| 3,864,394 | 2/1975 | Via | 260/543 |
| 4,241,021 | 12/1980 | Skrzec | 422/143 |

Primary Examiner—Thomas G. Wiseman
Assistant Examiner—Frederick W. Pepper

[57] ABSTRACT

An improved method for preparing phenylphosphonous dihalide comprises reacting $PCl_3$ and benzene in an electrically heated fluid bed reactor.

3 Claims, 1 Drawing Figure

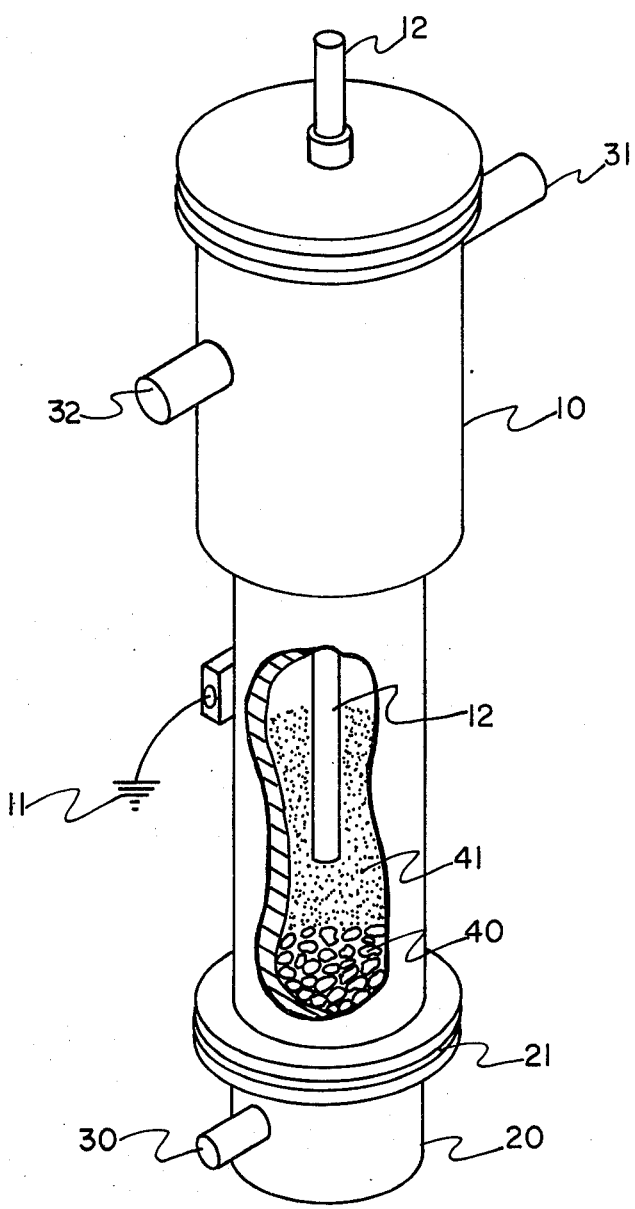
FIGURE

FLUID BED PROCESS FOR PREPARING PHENYLPHOSPHONOUS DICHLORIDE

BACKGROUND OF THE INVENTION

This invention relates to a process for the preparation of phenylphosphonous dichloride. More particularly, the present invention relates to a process for preparing phenylphosphonous dichloride in an electrically-heated fluid-bed reactor.

Phenylphosphonous dichloride is an important industrial intermediate which is used in the manufacture of the insecticide EPN, in the manufacture of nylon stabilizers and in the manufacture of organophosphorous compounds.

Of the several known methods by which phenylphosphonous dichloride can be prepared, the "hot tube" process and the "autoclave" process are perhaps the two most prominent.

In accordance with the basic hot tube process, benzene and phosphorous trichloride are vaporized to form a mixed vapor stream which is then caused to come into contact with the surface area of a "hot tube". The temperature of the surface of the hot tube is typically maintained at about 600° C. through the use of internal electrical heaters.

An improved hot-tube process, wherein monochlorobenzene is added to the reaction mixture, is taught in U.S. Pat. No. 3,029,282.

The basic autoclave process for preparing phenylphosphonous dichloride is described in U.S. Pat. No. 3,874,394, which also teaches that improved yields can be obtained by maintaining s specified relationship between reaction time, reaction temperature and the ratios of phosphorous trichloride and elemental phosphorous to monochlorobenzene present.

Each of these two processes are characterized by certain disadvantages. For example, the hot tube process is subject to formation of tarry residues (about 20-30 grams residue can be formed for every 100 grams phenylphosphonous dichloride produced), which can lead to fouling of downstream equipment, and has a tendency to generate undesirable byproducts such as biphenyl, chlorobenzenes and chlorophenyl phosphorous dichloride.

The Autoclave Process, on the other hand, involves a high pressure reaction (Ca 1000 psig) which may be regarded as an undesirable feature in and of itself.

A process which would enable the preparation of phenylphosphonous dichloride without the need to encounter the fouling potential characteristic of the hot tube process and without the need to operate at high pressure, such as is characteristic of the autoclave process, would be highly desirable.

It has now been found that phenylphosphonous dichloride can be prepared in an electrically heated fluid-bed reactor, in the absence of high pressure and with the coproduction of substantially less residue than that produced by the hot tube process.

SUMMARY OF THE INVENTION

In accordance with the present invention there is provided a process for preparing phenylphosphonous dichloride which comprises reacting benzene with phosphorous trichloride in an electrically heated fluidized bed reaction zone, the fluidized bed being comprised of inert electrically-conductive particles.

DESCRIPTION OF THE DRAWING

For a fuller understanding of the nature and objects of the invention reference should be had to the following detailed description taken in connection with the accompanying drawing representing a fluid-bed reactor which can be used in the practice of the present invention.

DETAILED DESCRIPTION OF THE INVENTION

In accordance with the present invention a vaporized feed stream of benzene and phosphorous trichloride is introduced into a fluidized bed of inert particulate matter maintained at a temperature sufficient to support a reaction between the benzene and phosphorous trichloride to form phenylphosphonous dichloride. Preferably, the fluidized bed is maintained at a temperature ranging from about 400° C. to about 650° C., although temperatures ranging from about 550° C. to about 600° C. are most preferred.

The vaporized feed stream is preferably supplemented with dry nitrogen in an amount which will render the total feed stream sufficient to support the fluidized bed and also provide the residence times desired. Air should be kept out of the reactor.

As the vapor passes through the fluid bed reaction zone, a reaction takes place whereupon a portion of the benzene and phosphorous trichloride react to form phenylphosphonous dichloride in accordance with the following equation:

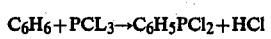

The product stream can then be charged directly to a product recovery system where the phenylphosphonous dihalide can be separated from the unreacted raw materials, which can then be recovered and recycled.

In practicing the process of the present invention, the initial vapor feed stream can be prepared in any of several ways known to those skilled in the art. Preferably, however, liquid benzene and phosphorous trichloride are premixed in the appropriate ratios, and then vaporized in a continuous vaporizer.

Monochlorobenzene, which can be added to the feed stream as a catalyst, can be added as a liquid or supplied directly to the reactor as a vapor.

The amount of catalyst added can vary from about 2 molar percent to about 10 molar percent of the total feed, with a preferred range being from about 6 molar percent to about 8 molar percent.

The ratios of phosphorous trichloride to benzene charged to the process of the present invention can vary widely, but preferably is within the molar ratio range of from about 1.0 to about 2.5. Within this range, the higher ratios are preferred because less monochlorobenzene byproduct is produced at high ratios than at low ratios.

The amount of phosphorous trichloride which is converted to phenylphosphonous dichloride is sensitive to reaction temperature. The bulk reaction temperature (.e., the average temperature of the reaction mass) in accordance with the present invention ranges from about 400° C. to about 600° C., with preferred temperatures ranging from about 550° C. to about 600° C. It will, of course, be understood that localized reaction temperatures, such as may exist at the surface of a particle making-up the fluid bed, or as may exist between two or more particles as the result of an electrical arc between them, may be considerably higher.

Apart from the actual bulk reaction temperature in and of itself, the conversion of PCl3 to phenylphosphonous dichloride can be sensitive to the density of the electrical current passing through the fluid bed. This can be measured in terms of amperes per square inch of current-supplying electrode submerged in the fluid bed. The effect of current density on conversion is not fully understood, but it is postulated that electrical arcing may be a contributing factor and that electrical arcing increases with increasing electrical density. Either alternating current or direct current can be used.

Particulate matter which may be used for the fluid bed includes, but is not limited to calcined petroleum coke.

A typical calcined petroleum coke which can be used in the practice of the present invention has the following characteristics.

|  | Chemical Analysis | Screen Analysis | |
|---|---|---|---|
|  |  | U.S. Screen | % retained |
| Moisture | 0.03% max. | +35 Mesh | 5% |
| Ash | 0.5% max. | 60 Mesh | 20–40 |
| Volatiles | 0.4% max. | 80 Mesh | 10–30 |
| Sulfur | 0.8% max. | 100 Mesh | 10–30 |
| Fixed Carbon | 98.5% | 140 Mesh | 10–20 |
|  |  | 200 Mesh | 5% max. |

If the particle size is too fine, the rate of elutriation can increase to an unacceptable level, while if the average particle size becomes too great, the bed will become more difficult to fluidize.

The residence time of the reactive gases in the fluid bed reaction zone can be an important factor in determining the ultimate success of the process. Preferred residence times for the practice of the present invention range from about 2 to about 10 seconds, although residence times of from about 3 seconds to about 5 seconds are more preferred.

Longer residence times can increase the coproduction of undesirable byproducts, which both reduces raw material efficiency and also results in a less pure product. Shorter residence times can result in lower raw material conversions.

A preferred electrically heated fluid bed reactor for use in the practice of this invention is illustrated in the accompanying drawing.

In the drawing the electrically-heated fluid-bed reactor is comprised of a housing 10 which serves as a grounding electrode and is grounded through ground connection 11; an electrode 12 which passes through the center of the reactor housing, a windbox 20 having a gas distributor plate 21, a feed inlet 30 and product outlet 31. The lower portion of the reactor is packed with a "grog" 40, i.e., a refractory material such as silica, alumina or the like, which is inert and thermally stable. The "grog" provides an insulating barrier between the high temperature upper bed 41 and the gas distribution plate.

The upper bed 41 comprises carbon particles which make-up the fluid bed reaction zone. As is shown, electrode 12 is partially submerged in the upper bed.

The process is preferably initiated by introducing a stream of dry nitrogen gas into inlet 30 at a rate sufficient to "fluidize" carbon bed 41, and then an electrical current is caused to flow through electrode 12 and the fluidized bed in an amount sufficient to heat the fluidized bed to a predetermined temperature, such as 550° C. Although the practice of the present invention is not limited thereto, a single-phase 60 cycle transformer is a convenient source of electricity for electrode 12.

Elevated pressures are not required.

Once the fluidized bed reaches the predetermined temperature, a vapor feed stream of phosphorous trichloride and benzene, which can also include monochlorobenzene as catalyst, is introduced to inlet 30. The flow rate of nitrogen is then reduced to accommodate the vapor feed stream. As the vapor feed rate is increased or decreased, corresponding adjustments are made in the nitrogen feed rate so that the total mass rate through the reactor remains sufficient to maintain the desired degree of fluidity in the fluid bed. The nitrogen rate can also be adjusted to increase or decrease residence time.

The product stream is withdrawn from the reactor outlet 31, and the phenylphosphonous dihalide is recovered therefrom by conventional techniques.

The amount of residue which is produced as a byproduct of the process is relatively low, ranging from about 4 to about 6 grams per 100 grams benzene phosphonous dihalide. In addition, under certain conditions, the coproduction of chlorinated biphenyls can be virtually eliminated.

Thus, for example, as the reaction temperature is reduced to about 535°–540° C., the coproduction of chlorinated biphenyls can be substantially reduced. The conversion of phosphonous trichloride to phenylphosphonous dichloride per pass will also be reduced.

In order that the present invention be more fully understood, the following examples are given by way of illustration.

No specific details or enumeration contained therein should be construed as limitations to the present invention except insofar as they appear in the appended claims. All parts and percentages are by weight unless otherwise specifically designated.

EXAMPLES

A series of experiments were conducted in a reactor similar to that shown in the figure. The reactor was constructed of a 27 inch (68.5 cm) long section of 3 inch (7.6 cm) type 346 stainless steel pipe, having an upper disengaging section constructed of a 24 inch (57.6 cm) length of 6 inch (15.2 cm) carbon steel pipe. The top of the disengaging section was fitted with ¾ inch (1.9 cm) inlet, which was used to add back bed material lost by elutriation; and a ¾ inch (1.9 cm) reaction product outlet.

An inlet/windbox was flanged to the bottom of the reactor, and a 1/16 inch (0.158 cm) thick stainless steel distributor plate having 11 3/32 inch (0.24 cm) holes on triangular centers. Approximately 6 inches (15.2 cm) of ⅛ inch (0.32 cm) silica grog was packed on top of the distributor plate, and a calcined petroleum coke bed was loaded on top of the grog.

Entering through a flange at the top of the reactor disengaging section was a ½ inch (1.27 cm) graphite electrode, which was carefully placed so as to run through the centerline of the reactor. The electrode was connected to a single phase 60 cycle alternating current transformer.

The reactant mixtures were premixed and transferred to a stainless steel head tank from which the mixtures were gravity-fed through a direct reading rotameter to a continuous vaporizer. The vaporized feed was directed to the reactor windbox through an electrically traced pipe. The windbox was also electrically traced to prevent condensation.

When monochlorobenzene was used, it was fed in the liquid state directly to the windbox through the use of a simple metering pump. The sensible heat of the vapor feed stream was relied upon to vaporize the monochlorobenzene.

The reactor product gases were directed through a cyclone separator to a glass vertical condenser, cooled by carbon tetrachloride. The reactor outlet piping and the cyclone separator were electrically traced.

In starting-up the reactor, a steady stream of nitrogen gas was introduced into the reactor through the windbox, to fluidize the carbon bed. An electric current was passed through the fluidized bed to bring it up to operating temperature, and the electrical tracing throughout the system was turned on. Electrical power supplied to the bed ranged from about 1 kw. to about 1.5 kw.

The carbon beds used were generally about 12 inches (30.6 cm) deep in the static condition, and the electrode was generally submerged 6.5 inches (16.5 cm) into the bed from the top. When the bed was expanded by fluidization, the volume increased about 20%. The electrode area of submergence under these circumstances was estimated to be about 13 square inches (83.9 cm$^2$).

Once the system reached operating temperature, the vapor feed stream (at a temperature of about 80° C.) was introduced into the windbox (which had been preheated to a temperature of about 175° C.). The nitrogen flow was continued to maintain an inert purge, and the flow rate of the nitrogen was adjusted to achieve the desired reaction zone residence time.

Extreme care was exercised to prevent either the phenylphosphonous dichloride or any unreacted phosphorous trichloride from coming into contact with water, as a violent reaction could result.

The results of these runs are shown in Table 1.

TABLE 1

PRODUCTION OF PHENYLPHOSPHONOUS DIHALIDE IN ELECTRICALLY HEATED FLUID BED REACTOR

| Run No. | Carbon Bed | Static Bed Depth In. | Static Bed Depth Cm. | PCl$_3$/ C$_6$H$_6$ Mole Ratio | C$_6$H$_5$Cl In Feed (Wgt. %) |
|---|---|---|---|---|---|
| 1 | A | 12 | 30.5 | 2 | — |
| 2 | A | 12 | 30.5 | 2 | — |
| 3 | A | 12 | 30.5 | 2 | — |
| 4 | A | 12 | 30.5 | 2 | — |
| 5 | A | 12 | 30.5 | 1.3 | — |
| 6 | B* | 12 | 30.5 | 1.3 | — |
| 7 | B | 12 | 30.5 | 1.3 | — |
| 8 | B | 12 | 30.5 | 2.0 | 3.7 |
| 9 | B | 12 | 30.5 | 2.0 | 8 |
| 10 | C* | 12 | 30.5 | 2.0 | 3.5 |

TABLE 1-continued
PRODUCTION OF PHENYLPHOSPHONOUS DIHALIDE IN ELECTRICALLY HEATED FLUID BED REACTOR

| | | | | | |
|---|---|---|---|---|---|
| | " | " | " | " | " |
| | " | " | " | " | " |
| | " | " | " | " | " |
| | " | " | " | " | " |
| | " | " | " | " | " |
| | " | " | " | " | " |
| | " | " | " | " | " |
| 11 | C | 12 | 30.5 | 2.0 | 3.8 |
| | " | " | " | " | " |
| | " | " | " | " | " |
| | " | " | " | " | " |
| | " | " | " | " | " |
| | " | " | " | " | " |
| | " | " | " | " | " |

| Run No. | Bed Temp. (°C.) | Superficial Gas Velocity Ft/sec. | Cm/sec. | Residence Time (sec.) |
|---|---|---|---|---|
| 1 | 550 | 0.22 | 6.71 | 5.34 |
| | 570 | 0.22 | 6.71 | 5.34 |
| | 600 | 0.285 | 8.69 | 5.1 |
| | 625 | 0.24 | 7.32 | 5.0 |
| 2 | 440 | 0.32 | 9.75 | 3.7 |
| | 500 | 0.32 | 9.75 | 3.7 |
| | 550 | 0.31 | 9.45 | 3.9 |
| | 600 | 0.32 | 9.75 | 3.7 |
| | 630 | 0.32 | 9.75 | 3.7 |
| 3 | 450 | 0.235 | 7.16 | 5.1 |
| | 500 | 0.304 | 9.27 | 3.9 |
| | 550 | 0.335 | 10.21 | 3.58 |
| | 575 | 0.31 | 9.45 | — |
| | 600 | 0.343 | 10.45 | 3.5 |
| | 625 | 0.335 | 10.21 | 3.58 |
| 4 | 450 | .265 | 8.08 | 4.5 |
| | 495 | .26 | 7.92 | 4.6 |
| | 550 | .26 | 7.92 | 4.6 |
| | 575 | .27 | 8.23 | 4.45 |
| | 600 | .255 | 7.77 | 4.7 |
| | 625 | .22 | 6.71 | 5.5 |
| 5 | 440 | 0.202 | 6.16 | 5.9 |
| | 495 | 0.198 | 6.04 | 6.06 |
| | 555 | 0.22 | 6.71 | 5.44 |
| | 575 | 0.21 | 6.40 | 5.7 |
| | 600 | 0.216 | 6.58 | 5.55 |
| | 625 | 0.212 | 6.46 | 5.6 |
| 6 | 460 | 0.322 | 9.81 | 3.72 |
| | 500 | 0.322 | 9.81 | 3.72 |
| | 550 | 0.322 | 9.81 | 3.72 |
| | 575 | 0.31 | 9.45 | 3.87 |
| | 600 | 0.31 | 9.45 | 3.8 |
| | 625 | 0.31 | 9.45 | 3.8 |
| 7 | 450 | 0.28 | 8.53 | 4.29 |
| | 500 | 0.267 | 8.14 | 4.49 |
| | 550 | 0.267 | 8.14 | 4.49 |
| | 575 | 0.267 | 8.14 | 4.49 |
| | 600 | 0.26 | 7.9 | 4.63 |
| | 630 | 0.26 | 7.9 | 4.63 |
| 8 | 430 | .208 | 6.34 | 5.76 |
| | 475 | .204 | 6.22 | 5.88 |
| | 550 | .22 | 6.71 | 5.34 |
| | 560 | .22 | 6.71 | 5.34 |
| | 590 | .226 | 6.89 | 5.30 |
| | 615 | .237 | 7.22 | 5.07 |
| 9 | 440 | 0.21 | 6.40 | 5.65 |
| | 490 | 0.24 | 7.32 | 4.9 |
| | 535 | 0.26 | 7.92 | 4.67 |
| | 570 | 0.255 | 7.77 | 4.7 |
| | 600 | 0.204 | 6.22 | 5.88 |
| | 615 | 0.24 | 7.32 | 4.9 |
| 10 | 440 | 0.277 | 8.44 | 4.32 |
| | 500 | 0.294 | 8.96 | 4.08 |
| | 515 | 0.333 | 10.15 | 3.61 |
| | 550 | 0.312 | 9.51 | 3.84 |
| | 600 | 0.32 | 9.75 | 3.8 |
| | 615 | 0.294 | 8.96 | 4.08 |
| 11 | 515 | 0.32 | 9.75 | 3.72 |
| | 565 | 0.32 | 9.75 | 3.72 |
| | 590 | 0.31 | 9.45 | 3.84 |
| | 615 | 0.27 | 8.23 | 4.42 |
| | 640 | 0.26 | 7.92 | 4.56 |

| Run No. | Product Analysis Mole % | | | | | |
|---|---|---|---|---|---|---|
| | $PCl_3$ | $C_6H_6$ | $POCl_3$ | $C_6H_5Cl$ | $C_6H_4Cl_2$ | $P_4$ |
| 1 | 64.2 | 35.4 | 0.28 | 0.39 | 0.00 | 0.05 |
| | 63.2 | 33.9 | 0.11 | 1.06 | 0.00 | 0.19 |
| | 64.6 | 32.0 | 0.08 | 1.44 | 0.00 | 0.25 |
| | 59.9 | 30.6 | 0.12 | 3.14 | 0.08 | 0.81 |
| | 58.8 | 28.5 | 0.04 | 4.78 | 0.18 | 1.33 |

TABLE 1-continued
PRODUCTION OF PHENYLPHOSPHONOUS DIHALIDE IN ELECTRICALLY HEATED FLUID BED REACTOR

| Run No. | | | | | | |
|---|---|---|---|---|---|---|
| ↓ | 57.7 | 27.3 | 0.04 | 5.60 | 0.27 | 1.68 |
| ↓ | 56.4 | 25.4 | 0.02 | 7.31 | 0.42 | 2.08 |
| ↓ | 54.3 | 23.1 | 0.03 | 10.15 | 0.79 | 2.60 |
| 2 | 63.13 | 37.9 | 0.17 | 0.00 | 0.00 | 0.00 |
| ↓ | 64.69 | 35.7 | 0.51 | 0.00 | 0.00 | 0.00 |
| ↓ | 64.07 | 36.8 | 0.16 | 0.00 | 0.00 | 0.00 |
| ↓ | 64.72 | 36.0 | 0.20 | 0.00 | 0.00 | 0.00 |
| ↓ | 64.72 | 35.4 | 0.19 | 0.13 | 0.00 | 0.07 |
| ↓ | 64.47 | 35.2 | 0.14 | 0.23 | 0.00 | 0.10 |
| ↓ | 62.84 | 32.1 | 0.09 | 1.72 | 0.02 | 0.55 |
| ↓ | 63.32 | 33.6 | 0.06 | 0.97 | 0.00 | 0.30 |
| ↓ | 61.41 | 30.4 | 0.05 | 2.98 | 0.07 | 0.81 |
| ↓ | 61.31 | 29.9 | 0.05 | 3.23 | 0.09 | 0.92 |
| 3 | 66.4 | 33.2 | 0.88 | 0.00 | 0.00 | 0.00 |
| ↓ | 66.9 | 33.0 | 0.44 | 0.00 | 0.00 | 0.00 |
| ↓ | 67.4 | 32.7 | 0.19 | 0.00 | 0.00 | 0.00 |
| ↓ | 67.3 | 32.8 | 0.26 | 0.00 | 0.00 | 0.00 |
| ↓ | 67.2 | 31.4 | 0.15 | 0.04 | 0.00 | 0.02 |
| ↓ | 67.4 | 32.6 | 0.13 | 0.02 | 0.00 | 0.00 |
| ↓ | 67.1 | 31.9 | 0.21 | 0.16 | 0.00 | 0.05 |
| ↓ | 66.9 | 32.1 | 0.14 | 0.17 | 0.00 | 0.04 |
| ↓ | 66.2 | 29.9 | 0.05 | 0.88 | 0.00 | 0.21 |
| ↓ | 65.6 | 27.4 | 0.04 | 0.84 | 0.00 | 0.21 |
| ↓ | 64.4 | 29.8 | 0.07 | 1.65 | 0.00 | 0.30 |
| ↓ | 65.0 | 29.7 | 0.06 | 1.78 | 0.00 | 0.44 |
| 4 | 65.94 | 33.5 | 0.31 | 0.28 | 0.00 | 0.00 |
| ↓ | 65.78 | 34.5 | 0.38 | 0.00 | 0.00 | 0.00 |
| ↓ | 66.14 | 34.3 | 0.20 | 0.00 | 0.00 | 0.00 |
| ↓ | 66.23 | 34.1 | 0.24 | 0.00 | 0.00 | 0.00 |
| ↓ | 65.92 | 34.4 | 0.27 | 0.00 | 0.00 | 0.00 |
| ↓ | 65.47 | 34.8 | 0.29 | 0.05 | 0.00 | 0.00 |
| ↓ | 65.34 | 34.7 | 0.24 | 0.09 | 0.00 | 0.09 |
| ↓ | 65.29 | 34.4 | 0.17 | 0.18 | 0.00 | 0.09 |
| ↓ | 64.02 | 32.8 | 0.08 | 1.02 | 0.01 | 0.25 |
| ↓ | 63.39 | 32.3 | 0.16 | 1.46 | 0.02 | 0.35 |
| ↓ | 64.76 | 29.3 | 0.09 | 1.67 | 0.03 | 3.43 |
| ↓ | 59.87 | 31.0 | 0.09 | 3.84 | 0.12 | 1.09 |
| 5 | 55.18 | 44.70 | 0.26 | 0.04 | 0.00 | 0.04 |
| ↓ | 55.18 | 44.70 | 0.26 | 0.04 | 0.00 | 0.04 |
| ↓ | 54.96 | 45.20 | 0.18 | 0.00 | 0.00 | 0.00 |
| ↓ | 55.21 | 44.96 | 0.14 | 0.00 | 0.00 | 0.00 |
| ↓ | 54.76 | 44.12 | 0.10 | 0.60 | 0.00 | 0.16 |
| ↓ | 54.62 | 44.70 | 0.10 | 0.38 | 0.00 | 0.09 |
| ↓ | 53.83 | 42.02 | 0.07 | 1.57 | 0.00 | 0.37 |
| ↓ | 50.60 | 41.24 | 0.06 | 3.12 | 0.06 | 0.82 |
| ↓ | 50.36 | 40.24 | 0.09 | 3.65 | 0.18 | 0.99 |
| ↓ | 50.85 | 37.99 | 0.00 | 4.40 | 0.12 | 1.10 |
| ↓ | 47.94 | 36.06 | 0.07 | 7.10 | 0.28 | 1.80 |
| ↓ | 47.58 | 35.80 | 0.00 | 7.68 | 0.29 | 2.05 |
| 6 | 54.60 | 45.46 | 0.33 | 0.00 | 0.00 | 0.00 |
| ↓ | 53.83 | 46.62 | 0.34 | 0.00 | 0.00 | 0.00 |
| ↓ | 54.07 | 46.11 | 0.30 | 0.00 | 0.00 | 0.00 |
| ↓ | 53.97 | 46.12 | 0.40 | 0.00 | 0.00 | 0.00 |
| ↓ | 54.56 | 45.62 | 0.18 | 0.06 | 0.00 | 0.00 |
| ↓ | 54.22 | 45.82 | 0.00 | 0.05 | 0.00 | 0.00 |
| ↓ | 53.97 | 45.81 | 0.08 | 0.27 | 0.00 | 0.10 |
| ↓ | 49.72 | 50.48 | 0.05 | 0.24 | 0.00 | 0.08 |
| ↓ | 48.78 | 49.55 | 0.00 | 0.84 | 0.00 | 0.24 |
| ↓ | 50.06 | 48.72 | 0.00 | 0.77 | 0.00 | 0.23 |
| ↓ | 44.88 | 49.89 | 0.00 | 2.50 | 0.00 | 0.66 |
| ↓ | 53.13 | 42.83 | 0.00 | 2.25 | 0.00 | 0.69 |
| 7 | 54.37 | 45.70 | 0.35 | 0.00 | 0.00 | 0.00 |
| ↓ | 54.98 | 45.24 | 0.19 | 0.00 | 0.00 | 0.00 |
| ↓ | 54.62 | 45.55 | 0.22 | 0.00 | 0.00 | 0.00 |
| ↓ | 53.08 | 47.26 | 0.18 | 0.00 | 0.00 | 0.00 |
| ↓ | 52.53 | 47.17 | 0.96 | 0.00 | 0.00 | 0.00 |
| ↓ | 55.29 | 44.60 | 0.22 | 0.07 | 0.00 | 0.00 |
| ↓ | 55.06 | 44.80 | 0.13 | 0.23 | 0.00 | 0.11 |
| ↓ | 54.74 | 44.82 | 0.14 | 0.21 | 0.00 | 0.16 |
| ↓ | 53.82 | 44.03 | 0.00 | 1.03 | 0.00 | 0.31 |
| ↓ | 53.68 | 43.51 | 0.07 | 1.00 | 0.00 | 0.29 |
| ↓ | 49.05 | 39.30 | 0.16 | 4.98 | 0.12 | 1.30 |
| ↓ | 49.08 | 42.73 | 0.09 | 4.43 | 0.09 | 1.35 |
| 8 | 65.33 | 33.60 | 0.00 | 1.03 | 0.00 | 0.00 |
| ↓ | 63.76 | 35.10 | 0.00 | 1.12 | 0.00 | 0.00 |
| ↓ | 65.27 | 33.85 | 0.00 | 0.88 | 0.00 | 0.00 |
| ↓ | 65.45 | 34.10 | 0.00 | 0.46 | 0.00 | 0.00 |
| ↓ | 60.84 | 29.87 | 0.00 | 2.02 | 0.30 | 1.00 |
| ↓ | 62.59 | 30.75 | 0.00 | 1.12 | 0.00 | 2.03 |
| ↓ | 61.43 | 29.93 | 0.00 | 2.56 | 0.10 | 1.62 |
| ↓ | 62.84 | 29.05 | 0.00 | 2.80 | 0.25 | 0.62 |
| ↓ | 60.56 | 28.55 | 0.00 | 3.73 | 0.35 | 1.60 |
| ↓ | 60.66 | 30.42 | 0.00 | 3.14 | 0.53 | 1.24 |
| ↓ | 62.60 | 29.45 | 0.00 | 2.64 | 0.40 | 1.20 |
| ↓ | 55.95 | 33.13 | 0.00 | 4.80 | 0.38 | 0.13 |
| 9 | 64.60 | 33.43 | 0.00 | 1.97 | 0.00 | 0.00 |
| ↓ | 64.79 | 32.99 | 0.00 | 2.22 | 0.00 | 0.00 |
| ↓ | 59.82 | 36.49 | 0.00 | 3.70 | 0.00 | 0.00 |
| ↓ | 61.90 | 35.19 | 0.00 | 2.90 | 0.00 | 0.00 |
| ↓ | 63.04 | 34.36 | 0.00 | 1.11 | 0.00 | 0.00 |
| ↓ | 62.58 | 33.03 | 0.00 | 1.87 | 0.00 | 0.00 |
| ↓ | 58.07 | 27.03 | 0.00 | 3.50 | 0.67 | 0.01 |
| ↓ | 55.90 | 27.00 | 0.00 | 4.60 | 0.78 | 1.30 |
| ↓ | 54.08 | 26.17 | 0.00 | 4.30 | 1.74 | 3.55 |
| ↓ | 55.65 | 28.14 | 0.00 | 4.90 | 1.53 | 0.95 |
| ↓ | 55.72 | 24.37 | 0.00 | 4.07 | 1.30 | 2.00 |
| ↓ | 56.65 | 24.12 | 0.00 | 5.10 | 1.16 | 1.87 |
| 10 | 64.27 | 35.51 | 0.00 | 0.21 | 0.00 | 0.00 |
| ↓ | 62.93 | 36.29 | 0.00 | 0.78 | 0.00 | 0.00 |
| ↓ | 63.51 | 36.14 | 0.00 | 0.34 | 0.00 | 0.00 |
| ↓ | 63.94 | 35.38 | 0.00 | 0.68 | 0.00 | 0.00 |
| ↓ | 63.97 | 35.02 | 0.00 | 0.72 | 0.00 | 0.00 |
| ↓ | 63.28 | 34.11 | 0.00 | 1.07 | 0.00 | 0.00 |
| ↓ | 64.11 | 33.59 | 0.00 | 0.78 | 0.00 | 0.00 |
| ↓ | 63.78 | 33.35 | 0.00 | 0.67 | 0.00 | 0.00 |
| ↓ | 60.65 | 29.02 | 0.00 | 2.63 | 0.15 | 0.43 |
| ↓ | 60.63 | 28.90 | 0.00 | 2.44 | 0.14 | 0.43 |
| ↓ | 55.94 | 30.00 | 0.00 | 5.40 | 0.45 | 1.00 |
| ↓ | 59.46 | 27.11 | 0.00 | 3.70 | 0.33 | 0.92 |
| 11 | 62.17 | 36.83 | 0.00 | 1.00 | 0.00 | 0.00 |
| ↓ | 64.09 | 35.08 | 0.00 | 0.69 | 0.00 | 0.00 |
| ↓ | 64.33 | 33.32 | 0.00 | 0.14 | 0.00 | 0.00 |
| ↓ | 64.26 | 32.86 | 0.00 | 0.42 | 0.00 | 0.00 |
| ↓ | 63.58 | 30.82 | 0.00 | 0.53 | 0.00 | 0.00 |
| ↓ | 63.18 | 30.35 | 0.00 | 0.44 | 0.07 | 0.09 |
| ↓ | 60.36 | 29.07 | 0.00 | 1.85 | 0.24 | 0.54 |
| ↓ | 60.49 | 28.18 | 0.00 | 2.10 | 0.23 | 0.52 |
| ↓ | 58.52 | 23.49 | 0.00 | 5.33 | 0.86 | 2.05 |
| ↓ | 58.17 | 23.52 | 0.00 | 5.40 | 0.95 | 2.25 |

| Run No. | Product Analysis Mole % | | |
|---|---|---|---|
| | $C_6H_5PCl_2$ | $(C_6H_5)_2$ | Chlorinated Biphenyls |
| 1 | 0.17 | 0.00 | 0.00 |
| ↓ | 1.96 | 0.00 | 0.00 |
| ↓ | 1.96 | 0.04 | 0.00 |
| ↓ | 5.56 | 0.21 | 0.00 |
| ↓ | 6.37 | 0.30 | 0.00 |
| ↓ | 6.75 | 0.49 | 0.00 |
| ↓ | 7.29 | 0.68 | 0.05 |
| ↓ | 7.19 | 1.09 | 0.10 |
| 2 | 0.00 | 0.00 | 0.00 |
| ↓ | 0.00 | 0.00 | 0.00 |
| ↓ | 0.00 | 0.00 | 0.00 |
| ↓ | 0.00 | 0.00 | 0.00 |
| ↓ | 0.39 | 0.00 | 0.00 |
| ↓ | 0.75 | 0.00 | 0.00 |
| ↓ | 3.12 | 0.04 | 0.00 |
| ↓ | 2.49 | 0.03 | 0.00 |
| ↓ | 4.73 | 0.11 | 0.00 |
| ↓ | 4.80 | 0.15 | 0.00 |
| 3 | 0.00 | 0.00 | 0.00 |
| ↓ | 0.00 | 0.00 | 0.00 |
| ↓ | 0.00 | 0.00 | 0.00 |
| ↓ | 0.00 | 0.00 | 0.00 |
| ↓ | 0.36 | 0.00 | 0.00 |
| ↓ | 0.15 | 0.00 | 0.00 |
| ↓ | 0.80 | 0.00 | 0.00 |
| ↓ | 0.96 | 0.00 | 0.00 |
| ↓ | 2.78 | 0.03 | 0.00 |
| ↓ | 2.56 | 0.00 | 0.00 |
| ↓ | 3.82 | 0.07 | 0.00 |
| ↓ | 4.08 | 0.05 | 0.00 |
| 4 | 0.00 | 0.00 | 0.00 |
| ↓ | 0.00 | 0.00 | 0.00 |
| ↓ | 0.00 | 0.00 | 0.00 |
| ↓ | 0.00 | 0.00 | 0.00 |
| ↓ | 0.00 | 0.00 | 0.00 |

TABLE 1-continued
PRODUCTION OF PHENYLPHOSPHONOUS DIHALIDE IN ELECTRICALLY HEATED FLUID BED REACTOR

|   |   |       |      |      |
|---|---|-------|------|------|
|   | ↓ | 0.00  | 0.00 | 0.00 |
|   | ↓ | 0.34  | 0.00 | 0.00 |
|   | ↓ | 0.09  | 0.00 | 0.00 |
|   | ↓ | 2.94  | 0.03 | 0.00 |
|   | ↓ | 2.83  | 0.04 | 0.00 |
|   | ↓ | 2.43  | 0.26 | 0.05 |
|   | ↓ | 4.27  | 0.07 | 0.10 |
| 5 | ↓ | 0.02  | 0.00 | 0.00 |
|   | ↓ | 0.02  | 0.00 | 0.00 |
|   | ↓ | 0.00  | 0.00 | 0.00 |
|   | ↓ | 0.00  | 0.00 | 0.00 |
|   | ↓ | 0.49  | 0.00 | 0.00 |
|   | ↓ | 0.43  | 0.00 | 0.00 |
|   | ↓ | 2.15  | 0.15 | 0.00 |
|   | ↓ | 4.23  | 0.15 | 0.00 |
|   | ↓ | 4.60  | 0.20 | 0.00 |
|   | ↓ | 5.29  | 0.26 | 0.00 |
|   | ↓ | 6.33  | 0.44 | 0.00 |
|   | ↓ | 6.03  | 0.48 | 0.11 |
| 6 |   | 0.00  | 0.00 | 0.00 |
|   | ↓ | 0.00  | 0.00 | 0.00 |
|   | ↓ | 0.00  | 0.00 | 0.00 |
|   | ↓ | 0.00  | 0.00 | 0.00 |
|   | ↓ | 0.00  | 0.00 | 0.00 |
|   | ↓ | 0.35  | 0.00 | 0.00 |
|   | ↓ | 0.18  | 0.00 | 0.00 |
|   | ↓ | 0.53  | 0.00 | 0.00 |
|   | ↓ | 1.66  | 0.00 | 0.00 |
|   | ↓ | 1.16  | 0.00 | 0.00 |
|   | ↓ | 3.35  | 0.08 | 0.00 |
|   | ↓ | 1.24  | 0.11 | 0.00 |
| 7 |   | 0.00  | 0.00 | 0.00 |
|   | ↓ | 0.00  | 0.00 | 0.00 |
|   | ↓ | 0.00  | 0.00 | 0.00 |
|   | ↓ | 0.00  | 0.00 | 0.00 |
|   | ↓ | 0.00  | 0.00 | 0.00 |
|   | ↓ | 0.10  | 0.00 | 0.00 |
|   | ↓ | 0.45  | 0.00 | 0.00 |
|   | ↓ | 0.26  | 0.00 | 0.00 |
|   | ↓ | 1.13  | 0.00 | 0.00 |
|   | ↓ | 1.74  | 0.00 | 0.00 |
|   | ↓ | 5.10  | 0.22 | 0.00 |
|   | ↓ | 2.48  | 0.23 | 0.00 |
| 8 |   | 0.00  | 0.00 | 0.00 |
|   | ↓ | 0.00  | 0.00 | 0.00 |
|   | ↓ | 0.34  | 0.00 | 0.00 |
|   | ↓ | 0.32  | 0.00 | 0.00 |
|   | ↓ | 5.33  | 0.00 | 0.00 |
|   | ↓ | 3.51  | 0.00 | 0.00 |
|   | ↓ | 4.29  | 0.00 | 0.00 |
|   | ↓ | 4.28  | 0.16 | 0.00 |
|   | ↓ | 4.97  | 0.13 | 0.00 |
|   | ↓ | 3.48  | 0.47 | 0.00 |
|   | ↓ | 3.46  | 0.22 | 0.00 |
|   | ↓ | 3.52  | 1.02 | 0.00 |
| 9 |   | 0.00  | 0.00 | 0.00 |
|   | ↓ | 0.00  | 0.00 | 0.00 |
|   | ↓ | 0.00  | 0.00 | 0.00 |
|   | ↓ | 0.00  | 0.00 | 0.00 |
|   | ↓ | 1.48  | 0.00 | 0.00 |
|   | ↓ | 2.52  | 0.00 | 0.00 |
|   | ↓ | 9.45  | 0.25 | 0.00 |
|   | ↓ | 10.20 | 0.31 | 0.00 |
|   | ↓ | 8.85  | 0.68 | 0.62 |
|   | ↓ | 7.80  | 0.58 | 0.40 |
|   | ↓ | 8.30  | 0.54 | 3.60 |
|   | ↓ | 9.86  | 0.67 | 0.53 |
| 10|   | 0.00  | 0.00 | 0.00 |
|   | ↓ | 0.00  | 0.00 | 0.00 |
|   | ↓ | 0.00  | 0.00 | 0.00 |
|   | ↓ | 0.00  | 0.00 | 0.00 |
|   | ↓ | 0.29  | 0.00 | 0.00 |
|   | ↓ | 1.53  | 0.00 | 0.00 |
|   | ↓ | 1.57  | 0.00 | 0.00 |
|   | ↓ | 2.19  | 0.00 | 0.00 |
|   | ↓ | 7.00  | 0.09 | 0.00 |
|   | ↓ | 7.30  | 0.17 | 0.00 |
|   | ↓ | 6.35  | 0.32 | 0.42 |
|   | ↓ | 8.30  | 0.29 | 0.00 |
| 11|   | 0.00  | 0.00 | 0.00 |
|   | ↓ | 0.14  | 0.00 | 0.00 |
|   | ↓ | 2.23  | 0.00 | 0.00 |
|   | ↓ | 2.44  | 0.00 | 0.00 |
|   | ↓ | 5.09  | 0.00 | 0.00 |
|   | ↓ | 5.80  | 0.05 | 0.00 |
|   | ↓ | 7.46  | 0.49 | 0.00 |
|   | ↓ | 7.74  | 0.73 | 0.00 |
|   | ↓ | 8.83  | 0.54 | 0.39 |
|   | ↓ | 8.76  | 0.65 | 0.30 |

*The bed was replaced with a new bed in kind.

These data demonstrate that benzene phosphonous dichloride is effectively and efficiently produced by the method of the present invention.

Run 1 shows that increasing bed temperatures results in increased conversion, although at temperatures about about 600° C. the coproduction of byproducts can become significant.

Runs 2 and 3 show that byproduct formation, even at higher temperatures, can be reduced by reducing residence times. Conversion is also reduced. These runs also demonstrate that phenyl phosphonous dichloride can be produced by the method of the present invention without the coproduction of chlorinated biphenyls.

Run 4 shows that when residence time is increased, conversion can also be increased, but at the expense of increased by-product formation at the higher temperatures.

Run 5 demonstrates that when the molar ratio of PCl$_3$ to benzene in the feed stream was reduced, conversion was also reduced.

Run 6 demonstrates that with the same molar ratio as was used in run 5, reduced residence times resulted in reduced conversions just as it had in the earlier runs with higher molar ratio feeds.

Run 7 demonstrates that with the same molar ratios as were used in runs 5 and 6, increased residence times resulted in increased conversions.

Runs 8–11 demonstrate that when monochlorobenzene is present in the feed stream, the conversions which can be achieved at lower temperatures are improved.

It will thus be seen that the objects set forth above are effectively attained and, since certain changes may be made in the above method without departing from the scope of the invention, it is intended that all matter contained in the above description shall be interpreted as illustrative and not in a limiting sense.

I claim:

1. A process for preparing phenylphosphonous dichloride which comprises reacting benzene with phosphorous trichloride at a temperature ranging from about 450° C. to about 600° C. in an electrically heated fluidized bed reaction zone comprising a fluidized bed of electrically-conductive particulate matter.

2. The process of claim 1 wherein said electrically-conductive particulate matter is carbon particles.

3. The process of claim 2 wherein said carbon particles are calcined petroleum coke.

* * * * *

UNITED STATES PATENT AND TRADEMARK OFFICE
CERTIFICATE OF CORRECTION

PATENT NO. : 4,436,673
DATED : March 13, 1984
INVENTOR(S) : Adam E. Skrzec

It is certified that error appears in the above-identified patent and that said Letters Patent is hereby corrected as shown below:

Col. 1, line 34, "s" should be -- a --;

Col. 1, lines 36 and 66, each occurrence of "phosphorous" should read -- phosphorus --;

Col. 1, lines 45 and 46 "phosphorous" should read --- phosphonous --;

Col. 2, lines 13, 16, 29, 42, 52 and 59, each occurrence of "phosphorous" should read -- phosphorus --;

Col. 2, line 33, "PCL$_3$" should be -- PCl$_3$ --;

Col. 2, line 62, ".e.," should be -- i.e., --;

Col. 4, line 31, "phosphonous" should read -- phosphorus --;

Col. 4, line 57, "5/8" should be -- 1/8 --;

Col. 12, line 24, "about" should be -- above --;

Col. 12, line 30 "phenyl phosphonous" should read -- phenylphosphonous --.

Signed and Sealed this

Eighteenth Day of December 1984

[SEAL]

Attest:

Attesting Officer

GERALD J. MOSSINGHOFF
Commissioner of Patents and Trademarks